(12) United States Patent
Chen

(10) Patent No.: US 8,928,097 B2
(45) Date of Patent: Jan. 6, 2015

(54) NOISE SHIELDING TECHNIQUES FOR ULTRA LOW CURRENT MEASUREMENTS IN BIOCHEMICAL APPLICATIONS

(71) Applicant: Genia Technologies, Inc., Mountain View, CA (US)

(72) Inventor: Roger J. A. Chen, Saratoga, CA (US)

(73) Assignee: Genia Technologies, Inc., Mountain View, CA (US)

( * ) Notice: Subject to any disclaimer, the term of this patent is extended or adjusted under 35 U.S.C. 154(b) by 9 days.

(21) Appl. No.: 13/972,616

(22) Filed: Aug. 21, 2013

(65) Prior Publication Data

US 2014/0027866 A1     Jan. 30, 2014

Related U.S. Application Data

(63) Continuation of application No. 13/396,522, filed on Feb. 14, 2012, now Pat. No. 8,541,849.

(51) Int. Cl.
*H01L 23/552*     (2006.01)
*H01L 49/02*     (2006.01)

(52) U.S. Cl.
CPC ............ *H01L 23/552* (2013.01); *H01L 28/60* (2013.01); *H01L 2924/0002* (2013.01)
USPC ........................................... 257/414

(58) Field of Classification Search
USPC .................. 257/414, 417, 423, 422
See application file for complete search history.

(56) References Cited

U.S. PATENT DOCUMENTS

| 2005/0009004 | A1* | 1/2005 | Xu et al. ......................... 435/4 |
| 2013/0146456 | A1* | 6/2013 | Gundlach et al. ............. 204/451 |
| 2013/0146457 | A1* | 6/2013 | Gundlach et al. ............. 204/451 |

* cited by examiner

*Primary Examiner* — Thao P Le
(74) *Attorney, Agent, or Firm* — Van Pelt, Yi & James LLP

(57) ABSTRACT

A device having an integrated noise shield is disclosed. The device includes a plurality of vertical shielding structures substantially surrounding a semiconductor device. The device further includes an opening above the semiconductor device substantially filled with a conductive fluid, wherein the plurality of vertical shielding structures and the conductive fluid shield the semiconductor device from ambient radiation. In some embodiments, the device further includes a conductive bottom shield below the semiconductor device shielding the semiconductor device from ambient radiation. In some embodiments, the opening is configured to allow a biological sample to be introduced into the semiconductor device. In some embodiments, the vertical shielding structures comprise a plurality of vias, wherein each of the plurality of vias connects more than one conductive layers together. In some embodiments, the device comprises a nanopore device, and wherein the nanopore device comprises a single cell of a nanopore array.

12 Claims, 4 Drawing Sheets

NOISE SHIELDING TECHNIQUES FOR ULTRA LOW CURRENT MEASUREMENTS IN BIOCHEMICAL APPLICATIONS

CROSS REFERENCE TO OTHER APPLICATIONS

This application is a continuation of U.S. patent application Ser. No. 13/396,522, entitled NOISE SHIELDING TECHNIQUES FOR ULTRA LOW CURRENT MEASUREMENTS IN BIOCHEMICAL APPLICATIONS filed Feb. 14, 2012 which is incorporated herein by reference for all purposes.

BACKGROUND OF THE INVENTION

Advances in micro-miniaturization within the semiconductor industry in recent years have enabled biotechnologists to pack traditionally bulky sensing tools into smaller and smaller form factors, onto so-called biochips. As device dimensions shrink, it would be desirable to develop high sensitivity measurement techniques for biochips.

BRIEF DESCRIPTION OF THE DRAWINGS

Various embodiments of the invention are disclosed in the following detailed description and the accompanying drawings.

DETAILED DESCRIPTION

Figure 1:
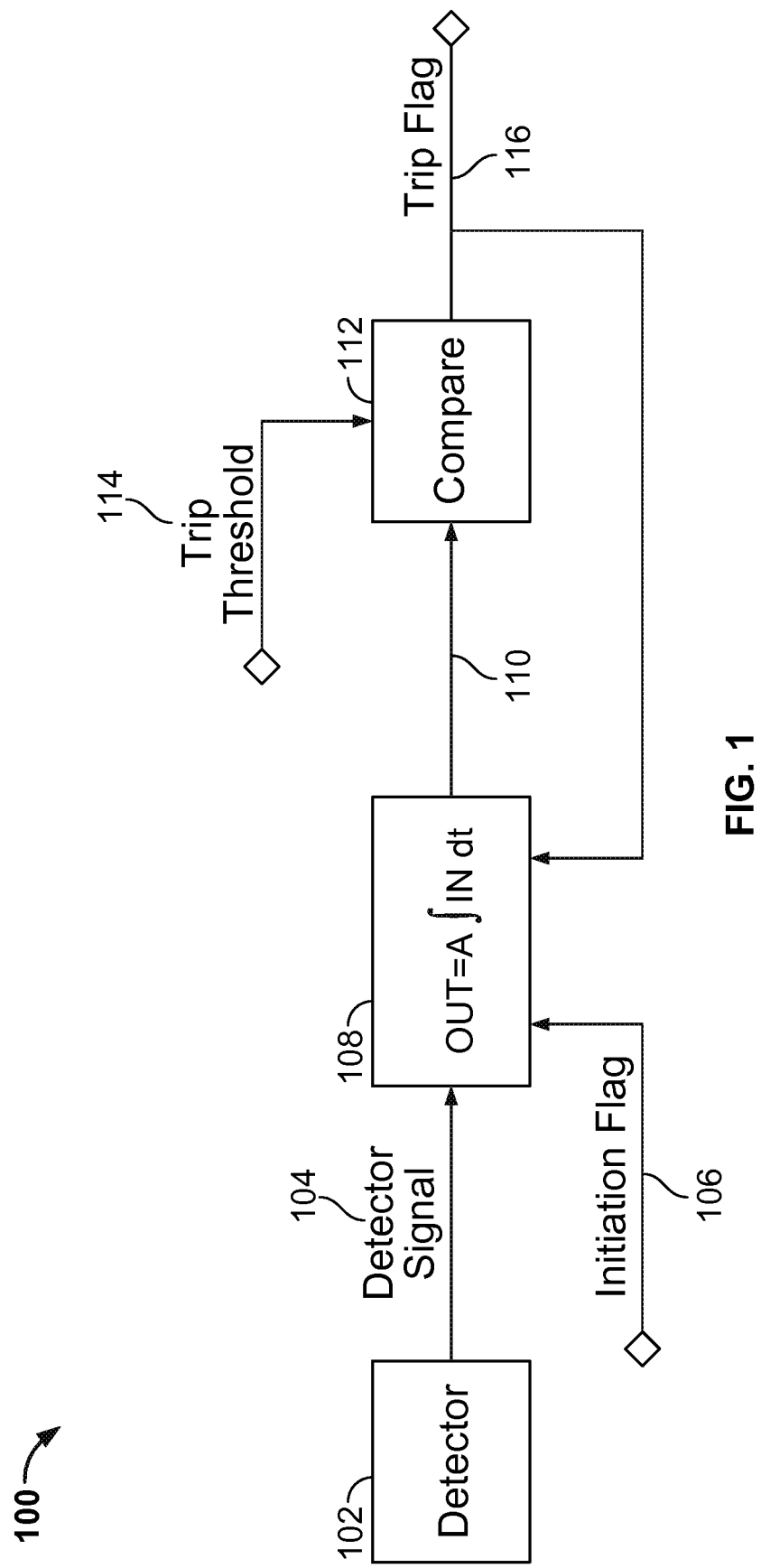
FIG. 1 is a block diagram illustrating an embodiment of a sensor circuit 100 for measuring a physical property, such as a current, voltage, or charge, within a single cell of a bio-sensor array using an integrating amplifier.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of 1 nanometer in internal diameter have shown promise in rapid nucleotide sequencing. A nanopore is a very small hole, and the nanopore can be created by a pore-forming protein or as a hole in synthetic materials, such as silicon or graphene. When a voltage potential is applied across the nanopore immersed in a conducting fluid, a small ionic current arising from the conduction of ions across the nanopore can be observed. When a molecule, such as a DNA or RNA molecule, passes through the nanopore, the molecule can partially or completely block the nanopore. Since the size of the ionic current is sensitive to the pore size, the blockage of the nanopore by the DNA or RNA molecule causes a change in the magnitude of the current through the nanopore. It has been shown that the ionic current blockage can be correlated with the base pair sequence of the DNA molecule.

However, molecule characterization using nanopore membrane devices face various challenges. One of the challenges is measuring very low-level signals: the magnitude of the ionic current through the nanopore is very low, typically on the order of a few tens or hundreds of picoamps (pA). Therefore, detecting any changes in such a low-level current through the nanopore becomes very challenging.

One effective circuit technique for measuring low-level current is using an integrating amplifier. Using an integrating amplifier to measure low-level current has several advantages. The integrating amplifier averages the current over many measurement periods, which helps mitigate the effects of noise to some degree. The integrating amplifier also limits the bandwidth to the bandwidth of interest without the need for additional filtering. The circuitry for the integrating amplifier at the measurement site is also small as compared to those corresponding to other measurement techniques, thus making it feasible to fabricate a bio-sensor array with a large array of measurement cells, which is highly desirable for identifying molecules in applications such as single strand DNA characterization.

FIG. 1 is a block diagram illustrating an embodiment of a sensor circuit 100 for measuring a physical property, such as a current, voltage, or charge, within a single cell of a bio-sensor array using an integrating amplifier. As shown in FIG. 1, a physical property is detected by detector 102 as detected signal 104. Sensor circuit 100 may be used to measure the mean value of detected signal 104 without sampling, as described further below.

In some embodiments, an initiation flag 106 resets an integrating amplifier 108 and starts a continuous integration of detected signal 104 over time. Integrated output 110 is compared with a trip threshold 114 using a comparator 112. When integrated output 110 reaches trip threshold 114, a trip flag 116 may be used as a feedback signal to integrating amplifier 108 for terminating the integration of detected signal 104. For example, when trip flag 116 is "on" or asserted, the integration is terminated. The duration of time between the assertion of initiation flag 106 and the assertion of trip flag 116 is proportional to the mean value of detected signal 104, e.g., the mean value of a current. Accordingly, the "on" and "off" of trip flag 116 (only 1 bit of information) may be sent from the cell to an external processor for calculating the mean value of detected signal 104. Alternatively, the "on/off" information may be sent from the cell to an external storage for delayed processing. For example, the clock cycles at which initiation flag 106 and trip flag 116 are respectively asserted may be recorded in an external storage. The number of clock cycles between the two asserted flags may then be used to determine the mean value of detected signal 104 at a later time.

In some embodiments, more accurate results may be obtained by integrating detected signal 104 over multiple integrating cycles. For example, the determined mean value of detected signal 104 may be further averaged over multiple integrating cycles. In some embodiments, initiation flag 106 is based at least in part on trip flag 116. For example, initiation flag 106 may be re-asserted in response to trip flag 116 being asserted. In this example, trip flag 116 is used as a feedback signal for reinitializing integrating amplifier 108, such that another cycle of integration of detected signal 104 may begin as soon as the previous cycle of integration is terminated. Re-asserting initiation flag 106 immediately after trip flag 116 is asserted reduces the portion of time when detector 102 generates a signal that is not integrated and thus not measured. The integration occurs over approximately the entire time that the signal is available. As a result, most of the information of the signal is captured, thereby minimizing the time to obtain an average value for the measured signal.

The sensitivity of sensor circuit 100 is maximized by continuously integrating detected signal 102 without sampling. This serves to limit the bandwidth of the measured signal. With continuous reference to FIG. 1, trip threshold 114 and an integration coefficient A set the bandwidth of the measured signal. As integration coefficient A decreases or as trip threshold 114 increases, the measured signal bandwidth decreases.

However, the low-current measuring circuit is susceptible to different noise sources, including external noise sources and noise sources within the measuring circuit itself. External noise sources affecting the performance of the low-current measuring circuit are numerous, including alternating current (AC) line noise, ballast noise from florescent light fixtures, electromagnetic interference (EMI), and the like.

Internal noise sources affecting the performance of the low-current measuring circuit include voltage and noise components from the integrating amplifier, as well as resistive noise from the measurement source. These components are amplified by the noise gain of the integrator, which is equal to $(1+C_{in}/C_{fb})$, where $C_{in}$ is the total input capacitance, and $C_{fb}$ is the integration capacitor (i.e., the feedback capacitor ($C_{fb}$) for the integrating amplifier).

Figure 2:
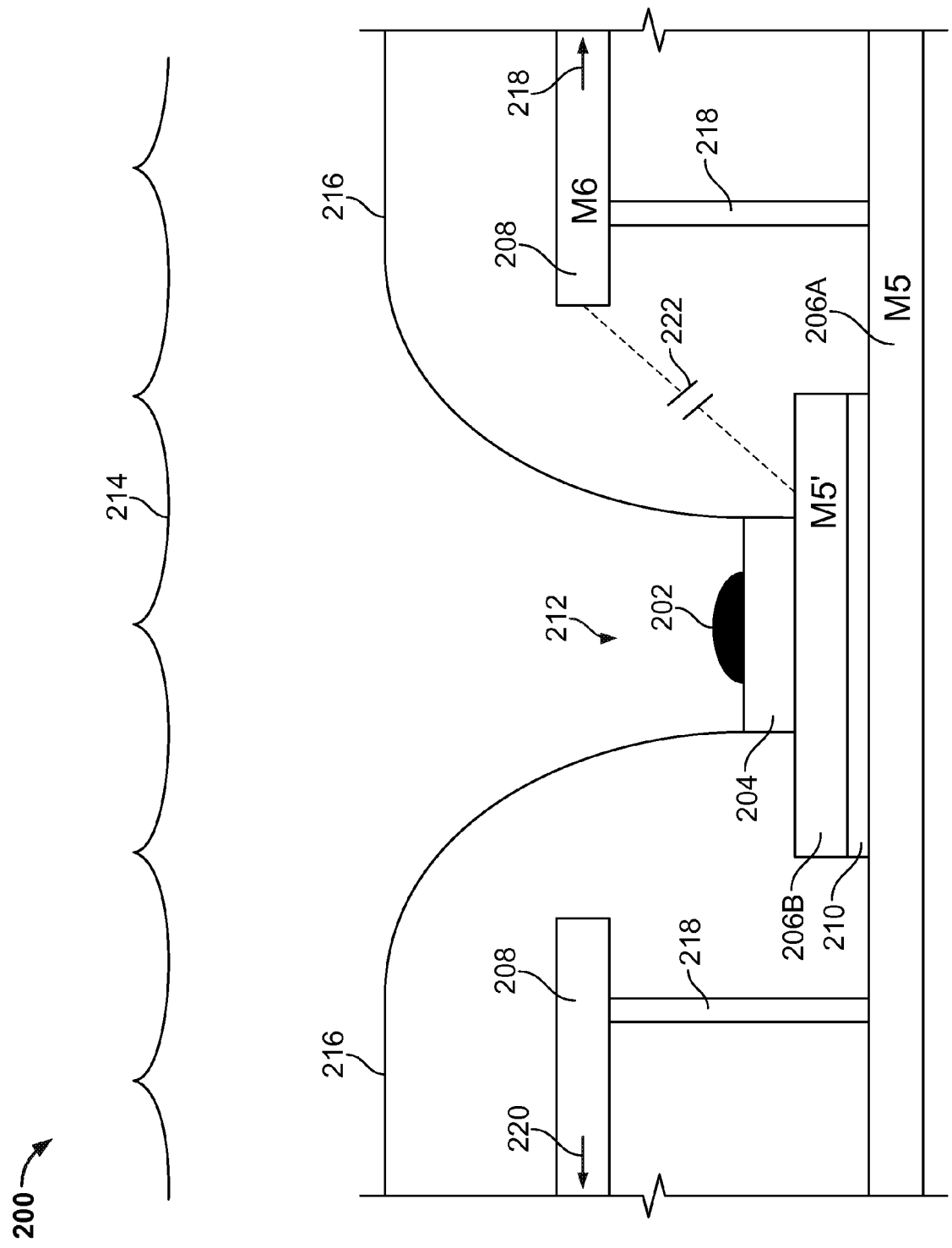
FIG. 2 is a diagram illustrating a cross-sectional view of an embodiment of a semiconductor device 200 with an integrated noise shield.

FIG. 2 is a diagram illustrating a cross-sectional view of an embodiment of a semiconductor device 200 with an integrated noise shield. In some embodiments, semiconductor device 200 is a nanopore device in a single cell of a nanopore array, and the integrated noise shield shields the nanopore device from both external noise sources and internal noise sources. In some embodiments, the integrated noise shield disclosed herein can also be integrated into other types of bio-sensor semiconductor arrays, such as bio-sensor semiconductor arrays in which low-level signal measurements susceptible to different noise sources are made. A nanopore device is used hereinafter as an example for semiconductor device 200. However, a nanopore device is selected for illustration purposes only; accordingly, the present application is not limited to this specific example only.

The integrated noise shield surrounds and shields the portions of semiconductor device 200 that are susceptible to different noise sources. For example, with continued reference to FIG. 2, the portions of semiconductor device 200 that are susceptible to noise include a biological sample 202, a measurement electrode 204, other measurement integrated circuitries (not shown in the figure), and the like, and these portions of semiconductor device 200 are surrounded and shielded by the integrated noise shield. The integrated noise shield can be formed using any conductive material.

The integrated noise shield includes a bottom shield. With continued reference to FIG. 2, the bottom shield includes one or more conductive layers (206A and 206B) that are placed below the portions of semiconductor device 200 that are susceptible to noise. In some embodiments, conductive layer 206A is metal layer 5 (M5), which is the metal layer below the top metal layer 208 (M6) of semiconductor device 200. Conductive layer 206B is metal layer 5' (M5' or MIM Cap layer), which is a metal layer sitting on top of M5 with a thin layer of oxide 210 in between. In some embodiments, the bottom shield is formed using conductive materials other than metal, including polycrystalline silicon, and the like. In some embodiments, semiconductor device 200 includes other conductive layers, such as a layer of substrate. Since the layer of substrate is typically thick and conductive, it acts as a bottom shield layer for semiconductor device 200.

The integrated noise shield includes a top shield. The top shield includes a conductive layer 208 with an opening 212. With continued reference to FIG. 2, the conductive layer 208 of the top shield is a metal layer placed above the portions of semiconductor device 200 that are susceptible to noise. In some embodiments, conductive layer 208 is metal layer 6 (M6), which is the top metal layer of semiconductor device 200. In some embodiments, opening 212 allows biological sample 202 to be introduced into semiconductor device 200 such that biological sample 202 can be tested or analyzed by semiconductor device 200.

The top shield further includes a conductive liquid shield 214 deposited over and covering the portions of semiconductor device 200 that are susceptible to noise, including biological sample 202. Without conductive liquid shield 214, opening 212 would expose semiconductor device 200 to different noise sources. In addition, conductive layer 208 (e.g., M6) cannot come into contact with the conductive liquid shield 214. Therefore, conductive layer 208 is covered with a layer of oxide 216 to insulate it from conductive liquid shield 214. In some embodiments, conductive liquid shield 214 is an electrolyte containing free ions that make the electrolyte electrically conductive.

The integrated noise shield further includes a side shield. The side shield includes a plurality of vertical shielding structures 218 forming a sidewall substantially surrounding the noise sensitive portions of semiconductor device 200. Note that in FIG. 2, only two vertical shielding structures 218 are illustrated. However, the number of vertical shielding structures 218 can be more than two as well. In some embodiments, vertical shielding structures 218 include vias. Vias are formed by etching holes in insulating materials and depositing tungsten or other conductive material in the etched holes. The vias are used to make vertical conductive connections between the various metal or other conductive layers of semiconductor device 200. For example, with reference to FIG. 2, vias 218 interconnect conductive layer 208 and conductive layer 206A.

The plurality of vertical shielding structures 218 can be arranged in different configurations to achieve maximum shielding. FIG. 3A is a diagram illustrating a top-view of an exemplary configuration of vertical shielding structures 218. As shown in FIG. 3A, the plurality of vertical shielding structures 218 (e.g., vias) can be arranged in a rectangular layout surrounding measurement electrode 204 and other noise sensitive portions of semiconductor device 200. However, other configuration shapes can be used as well. For example, the plurality of vertical shielding structures 218 can be arranged in a concentric ring surrounding measurement electrode 204 and other noise sensitive portions of semiconductor device 200.

Figure 3B:
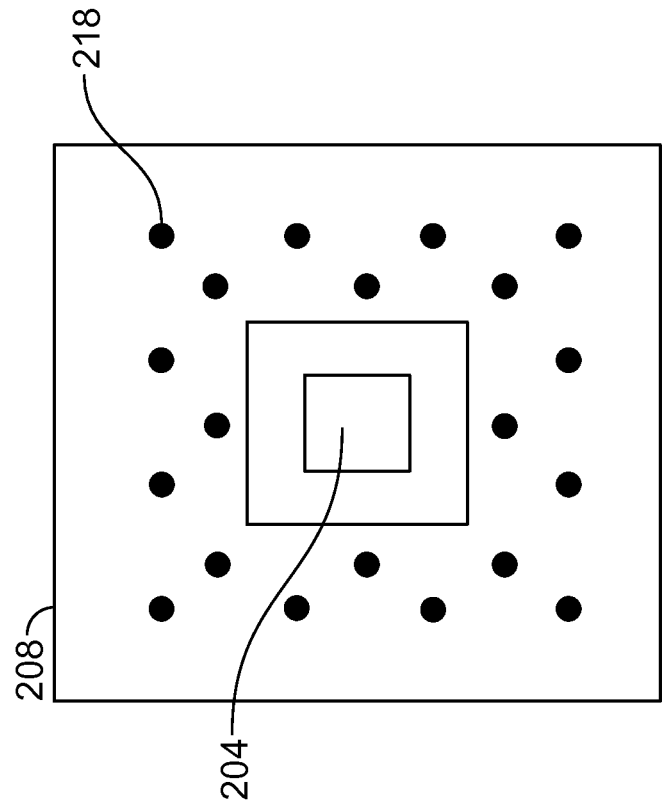
FIG. 3B is a second diagram illustrating a top-view of another exemplary configuration of vertical shielding structures 218.
Figure 3A:
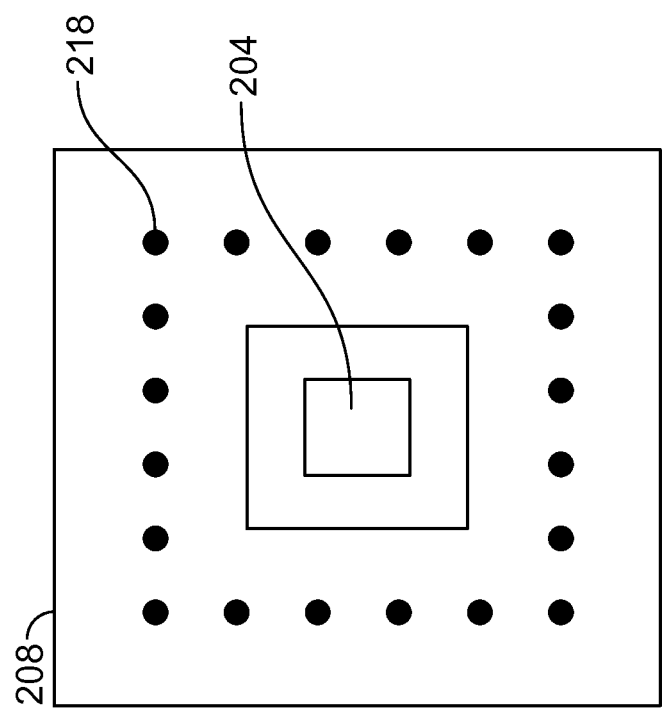
FIG. 3A is a diagram illustrating a top-view of an exemplary configuration of vertical shielding structures 218.

FIG. 3B is a second diagram illustrating a top-view of another exemplary configuration of vertical shielding structures 218. In this configuration, the plurality of vertical shielding structures 218 are arranged in a plurality of concentric squares or rings, e.g., two concentric squares. In some embodiments, the vertical shielding structures 218 in one ring are offset from the vertical shielding structures 218 in a different ring, i.e., the rings of vertical shielding structures 218 are not aligned together. While a single continuous shielding wall surrounding the noise sensitive portions of semiconductor device 200 may provide good shielding, the implementation of such a shielding wall may not be feasible due to various design or technical constraints. By offsetting one ring of vertical shielding structures 218 from another as shown in FIG. 3B, the shielding effect is close to that achieved by forming a single continuous shielding wall surrounding the noise sensitive portions of semiconductor device 200.

With continued reference to FIG. 2, conductive layer 208, which is a portion of the top shield, can be extended horizontally and radially outwards in the directions indicated by arrows 218 and 220, respectively. Extending conductive layer 208 outwardly in this manner creates a roof edge or awning shielding, which can further prevent some of the interference from passing through a plurality of gaps between the plurality of vertical shielding structures 218.

In some embodiments, the amount of extension of conductive layer 208 described above can be traded off against the density of the plurality of vertical shielding structures 218. Vias are typically made of tungsten, and polishing tungsten becomes more challenging when the vias are more densely populated. Therefore, in some embodiments, the plurality of vertical shielding structures 218 can be spaced further apart when conductive layer 208 is extended further outward to form an expanded roof edge or awning to prevent some of the interference from infiltrating in between the plurality of vertical shielding structures 218.

In some embodiments, some of the conductive layers or oxide layers forming the integrated shield of semiconductor device 200 are exploited to form a capacitor. For example, as shown in FIG. 2, the oxide layer 210 between M5' and M5 forms a capacitor 222. In some embodiments, semiconductor device 200 requires capacitors for various purposes. For example, the integrating amplifier in semiconductor device 200 may require a capacitance, which can be provided by capacitor 222.

Figure 4:
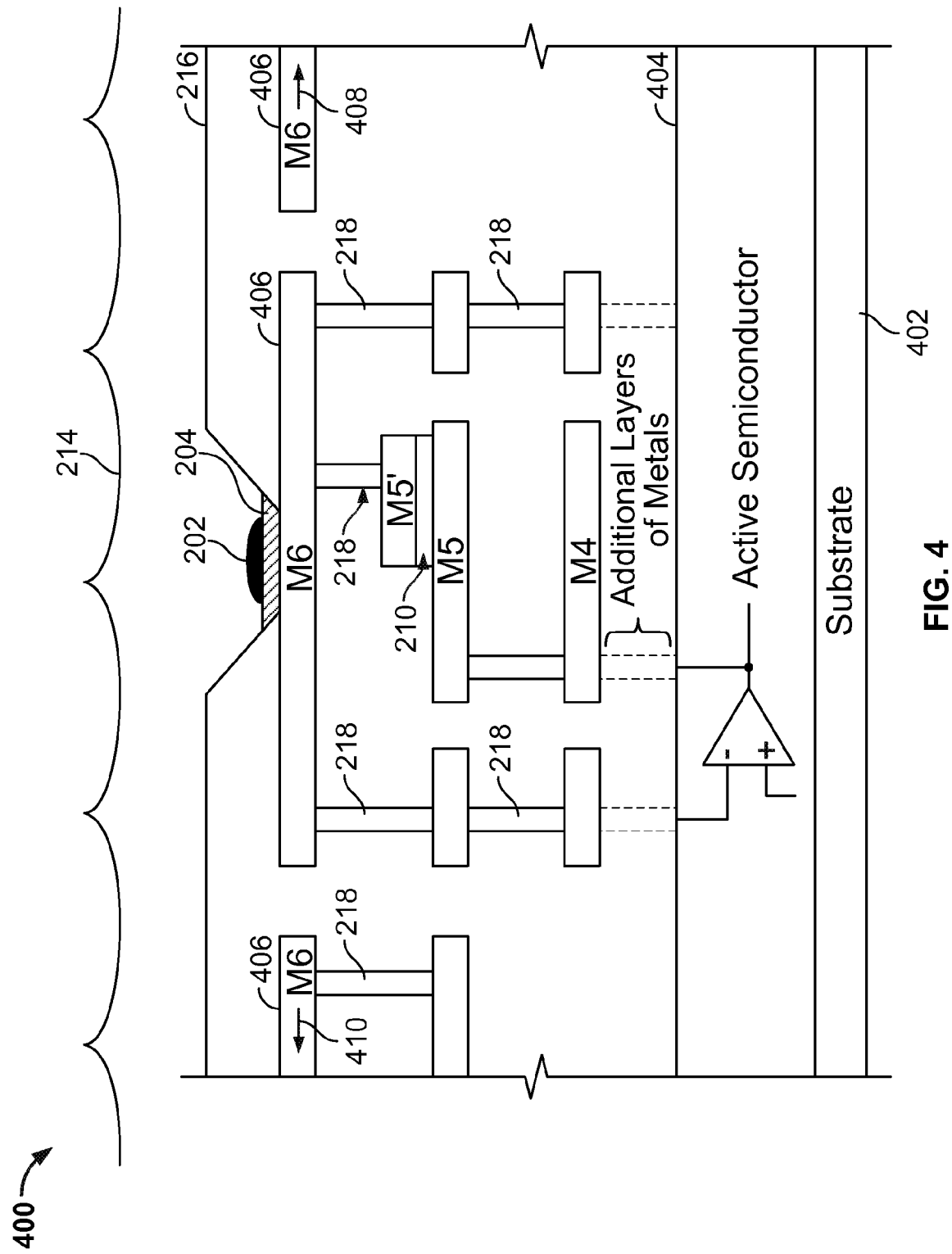
FIG. 4 is a diagram illustrating a cross-sectional view of an embodiment of a semiconductor device 400 with an integrated noise shield.

FIG. 4 is a diagram illustrating a cross-sectional view of an embodiment of a semiconductor device 400 with an integrated noise shield. The integrated noise shield surrounds and shields the portions of semiconductor device 400 that are susceptible to different noise sources.

The integrated noise shield includes a bottom shield. With continued reference to FIG. 4, the bottom shield includes a substrate layer 402 that is placed below the portions of semiconductor device 400 that are susceptible to noise, including a layer 404 containing active semiconductor circuits.

The integrated noise shield includes a top shield. In this embodiment, the top shield includes a conductive liquid shield 214 deposited over and covering the portions of semiconductor device 400 that are susceptible to noise, including biological sample 202. Conductive layer 406 (e.g., M6) cannot come into contact with conductive liquid shield 214. Therefore, conductive layer 406 is covered with a layer of oxide 216 to insulate it from conductive liquid shield 214, which may be an aqueous electrolyte solution as described earlier.

The integrated noise shield further includes a side shield. The side shield includes a plurality of vertical shielding structures 218 (e.g., vias) forming a sidewall substantially surrounding the noise sensitive portions of semiconductor device 400.

The plurality of vertical shielding structures 218 can be arranged in different configurations to achieve maximum shielding. For example, configurations similar to those in FIG. 3A and FIG. 3B may be used.

With continued reference to FIG. 4, conductive layer 406 can be extended radially outwards in the directions indicated by arrows 408 and 410, respectively. Extending conductive layer 406 outwards in this manner creates a roof edge or awning, which can prevent some of the interference from infiltrating in between the plurality of vertical shielding structures 218. In some embodiments, the amount of extension of conductive layer 406 described above can be traded off against the density of the plurality of vertical shielding structures 218.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A device comprising:
   a. nanopore device comprising a nanopore disposed in a membrane;
   b. a sensor circuit in proximity to the nanopore disposed in the membrane; and
   c. a cavity substantially filled with a conductive liquid;
   wherein the conductive liquid shields the nanopore device from radiation.

2. The device of claim 1, wherein the cavity substantially filled with the conductive liquid is above the sensor circuit.

3. The device of claim 1, wherein the cavity is further coupled to an opening to allow a biological sample to be introduced into the cavity.

4. The device of claim 1, wherein the conductive liquid comprises an electrolyte.

5. The device of claim 1, wherein the nanopore device comprises a single cell of a nanopore array.

6. The device of claim 1, further comprising a layer of oxide insulating the conductive liquid from a portion of the device.

7. A method for shielding a nanopore device from radiation, comprising:
   providing a sensor circuit in proximity to a nanopore disposed in a membrane;
   providing a cavity substantially filled with a conductive liquid; and
   wherein the conductive liquid shields the nanopore device from radiation.

8. The method of claim 7, wherein the cavity substantially filled with the conductive liquid is above the sensor circuit.

9. The method of claim 7, further providing an opening coupled to the cavity, wherein the opening allows a biological sample to be introduced into the cavity.

10. The method of claim 7, wherein the conductive liquid comprises an electrolyte.

11. The method of claim 7, wherein the nanopore device comprises a single cell of a nanopore array.

12. The method of claim 7, further providing a layer of oxide insulating the conductive liquid from a portion of the nanopore device.

* * * * *